United States Patent
Shimizu et al.

(10) Patent No.: US 11,361,917 B2
(45) Date of Patent: Jun. 14, 2022

(54) OPERATION SWITCH AND ENDOSCOPE

(71) Applicant: OLYMPUS CORPORATION, Tokyo (JP)

(72) Inventors: Masami Shimizu, Hachioji (JP); Shigeyasu Kishioka, Kunitachi (JP); Yoki Onishi, Hachioji (JP); Toshihiko Suzuta, Inagi (JP)

(73) Assignee: OLYMPUS CORPORATION, Tokyo (JP)

( * ) Notice: Subject to any disclaimer, the term of this patent is extended or adjusted under 35 U.S.C. 154(b) by 297 days.

(21) Appl. No.: 16/866,608

(22) Filed: May 5, 2020

(65) Prior Publication Data

US 2020/0266009 A1 Aug. 20, 2020

Related U.S. Application Data

(63) Continuation of application No. PCT/JP2018/030508, filed on Aug. 17, 2018.

(30) Foreign Application Priority Data

Nov. 17, 2017 (JP) .............................. JP2017-221726

(51) Int. Cl.
*H01H 13/06* (2006.01)
*A61B 1/00* (2006.01)
*H01H 13/14* (2006.01)

(52) U.S. Cl.
CPC .......... *H01H 13/06* (2013.01); *A61B 1/00039* (2013.01); *H01H 13/14* (2013.01); *A61B 1/00052* (2013.01); *H01H 2217/01* (2013.01)

(58) Field of Classification Search
CPC .... H01H 13/06; H01H 2223/002; H01H 9/04; H01H 13/86; H01H 2009/048;
(Continued)

(56) References Cited

U.S. PATENT DOCUMENTS 5,367,133 A * 11/1994 Schmidt ................. H01H 13/14
200/309
5,545,865 A 8/1996 Gotou
(Continued)

FOREIGN PATENT DOCUMENTS

CN 101877291 A 11/2010
CN 105679583 A 6/2016
(Continued)

OTHER PUBLICATIONS

International Search Report dated Nov. 20, 2018 issued in International Application No. PCT/JP2018/030508.

*Primary Examiner* — Ahmed M Saeed
(74) *Attorney, Agent, or Firm* — Scully, Scott, Murphy & Presser, P.C.

(57) ABSTRACT

An operation switch includes a concave portion in which an inner peripheral surface is constituted by a first inclined surface that is reduced in diameter toward a bottom portion from an external surface of a frame and a cylindrical portion that is formed in a pressing type operation button mounted on the concave portion and in which an outer peripheral surface is constituted by a second inclined surface that has a gradient larger than a gradient of the first inclined surface and faces the inner peripheral surface of the concave portion.

10 Claims, 8 Drawing Sheets

(58) Field of Classification Search
CPC ...... H01H 13/063; H01H 21/08; H01H 23/06;
H01H 3/125; H01H 13/705; H01H 13/14;
H01H 13/04; H01H 13/10; H01H 13/70;
H01H 13/704; H01H 13/7065; H01H
13/7006; H01H 13/7057; H01H 13/78;
H01H 13/79; H01H 13/52; H01H 13/703;
H01H 13/507; H01H 3/12; H01H 13/20
See application file for complete search history.

(56) References Cited

U.S. PATENT DOCUMENTS

| | | | | |
|---|---|---|---|---|
| 5,930,545 | A | * | 7/1999 | Petruchik ............... G03B 17/38 396/542 |
| 8,939,489 | B2 | * | 1/2015 | Oeuvrard ............ B60R 13/0256 296/1.08 |
| 2007/0219409 | A1 | | 9/2007 | Shimizu et al. |

FOREIGN PATENT DOCUMENTS

| | | |
|---|---|---|
| EP | 1 836 945 A2 | 9/2007 |
| JP | S48-047230 U | 6/1973 |
| JP | S63-029827 U | 2/1988 |
| JP | H06-267370 A | 9/1994 |
| JP | H07239992 A | 9/1995 |
| JP | 2004-172133 A | 6/2004 |
| JP | 2007-252419 A | 10/2007 |

* cited by examiner

OPERATION SWITCH AND ENDOSCOPE

CROSS REFERENCE TO RELATED APPLICATION

This application is a continuation application of PCT/JP2018/030508 filed on Aug. 17, 2018 and claims benefit of Japanese Application No. 2017-221726 filed in Japan on Nov. 17, 2017, the entire contents of which are incorporated herein by this reference.

BACKGROUND OF THE INVENTION

1. Field of the Invention

The present invention relates to an operation switch and an endoscope, the operation switch being used for an endoscope or a coupling device for endoscope, such as an image pickup apparatus or a display apparatus, coupled to an endoscope.

2. Description of the Related Art

Conventionally, an endoscope has been used in order to observe a part to be inspected in a subject or perform various treatments using a treatment instrument inserted into a treatment instrument channel, if necessary, by inserting an elongated insertion portion into the subject such as a body cavity.

In the above-described endoscope, an endoscope including a push-button type operation switch provided on an operation portion continuously provided at a proximal end of the insertion portion in order to perform an operation regarding various functions of the endoscope by hand has been known. Further, in the coupling device for endoscope such as the image pickup apparatus or display apparatus that can be coupled to the endoscope, an endoscope including a similar operation switch has been known.

The endoscope, the coupling device for endoscope, or the like needs a waterproof property particularly when used for a medical care. Accordingly, a configuration in which a concave portion formed in an exterior member to house an operation button is water-tightly blocked by the operation button made of a material having elasticity such as a silicone material has been widely adopted for an operation switch for such an application.

For example, Japanese Patent Application Laid-Open Publication No. 2007-252419 discloses a switch mechanism (operation switch) in which an operation portion (operation button) in which a substantially column-shaped base and a deflection part extended to an outside in a radial direction from one end portion of the base are integrally formed by a material having elasticity such as a silicone rubber material are fitted into a concave portion formed in an exterior member. In the operation switch, the deflection portion can be caused to be elastically deformed by a pressing operation and the switch member provided inside the exterior member can be caused to be turned on and off by displacing the base.

SUMMARY OF THE INVENTION

An operation switch according to one aspect of the present invention includes a concave portion provided in an endoscope or an exterior member of a coupling device for endoscope in which a switch member is housed, the concave portion including, as an inner peripheral surface, a first inclined surface reduced in diameter toward a bottom portion from an external surface; a cylindrical portion formed on a pressing type operation button housed in the concave portion, the cylindrical portion including a second inclined surface on an outer peripheral surface, the second inclined surface facing the first inclined surface and being reduced in diameter by a gradient not less than a gradient of the first inclined surface in a same direction as a direction of the first inclined surface; and a convex portion for sealing in an annular shape, the convex portion for sealing projecting from the cylindrical portion and abutting on the concave portion.

Further, an operation switch according to another aspect of the present invention includes a concave portion provided in an endoscope or an exterior member of a coupling device for endoscope in which a switch member is housed, the concave portion including, as an inner peripheral surface, a first inclined surface reduced in diameter toward a bottom portion from an external surface; a cylindrical portion formed on a pressing type operation button housed in the concave portion, the cylindrical portion including a second inclined surface on an outer peripheral surface, the second inclined surface facing the first inclined surface and being reduced in diameter by a gradient not less than a gradient of the first inclined surface from one end on a side of the external surface in slide contact with the first inclined surface toward another end on a side of the bottom portion; and a convex portion for sealing in an annular shape, the convex portion for sealing projecting from the cylindrical portion and abutting on the concave portion.

Further, an endoscope according to one aspect of the present invention includes an exterior member that forms an exterior; a concave portion provided in the exterior member and including, as an inner peripheral surface, a first inclined surface reduced in diameter toward a bottom portion from an external surface; a cylindrical portion formed on a pressing type operation button housed in the concave portion, the cylindrical portion including a second inclined surface on an outer peripheral surface, the second inclined surface facing the first inclined surface and being reduced in diameter by a gradient not less than a gradient of the first inclined surface in a same direction as a direction of the first inclined surface; and a convex portion for sealing in an annular shape, the convex portion for sealing projecting from the cylindrical portion and abutting on the concave portion.

DETAILED DESCRIPTION OF THE PREFERRED EMBODIMENT(S)

Figure 3:
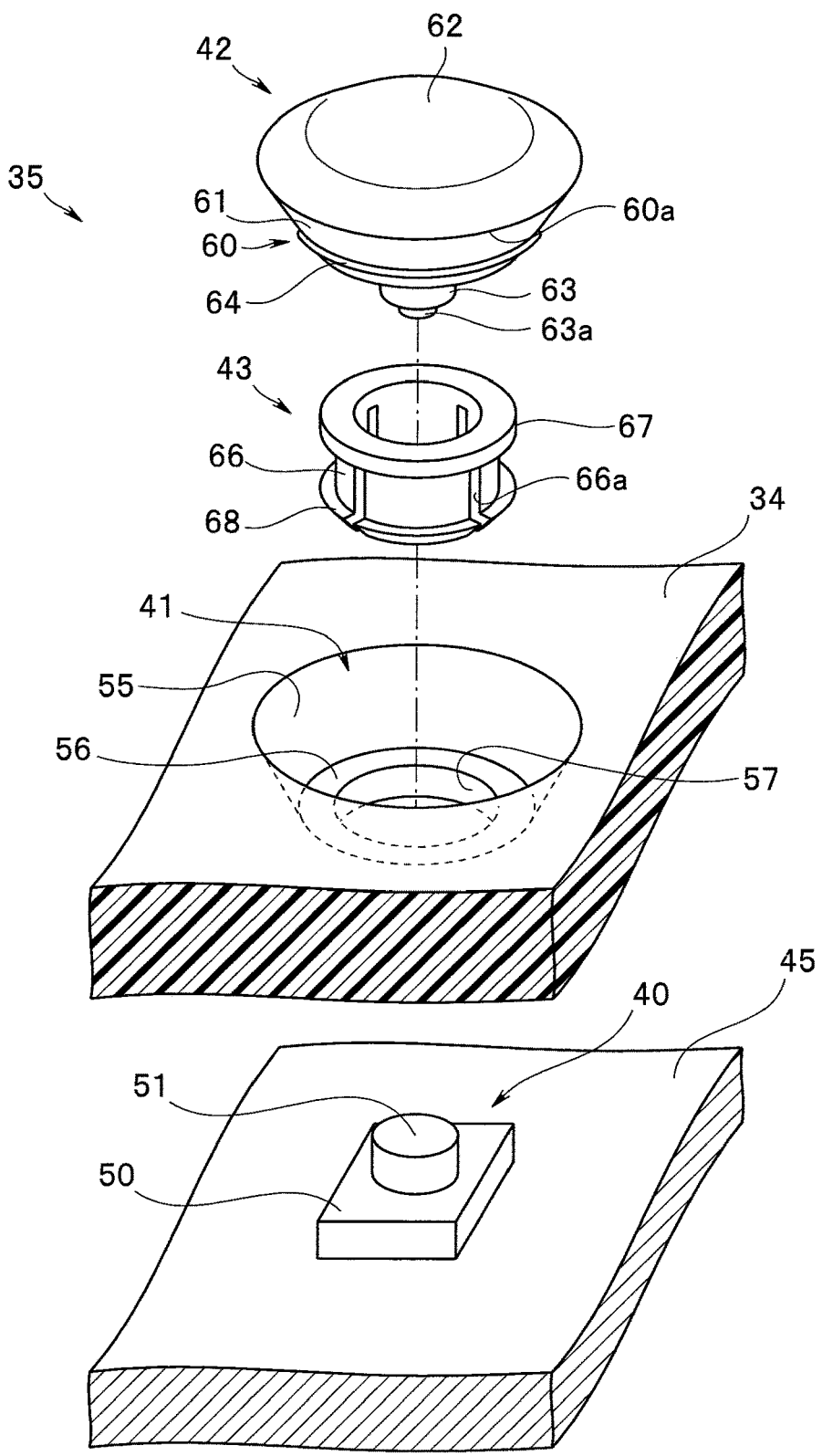
FIG. 3 is an exploded perspective view of an operation switch.
Figure 4:
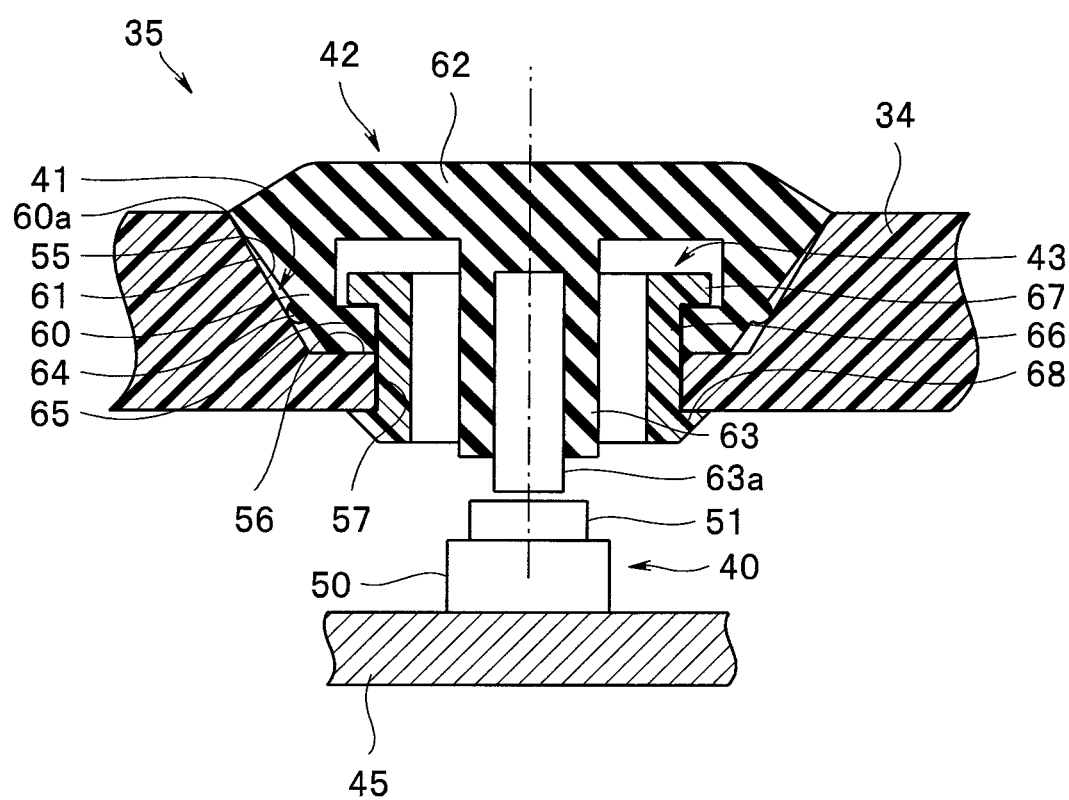
FIG. 4 is a main-part sectional view of the operation switch.
Figure 5:
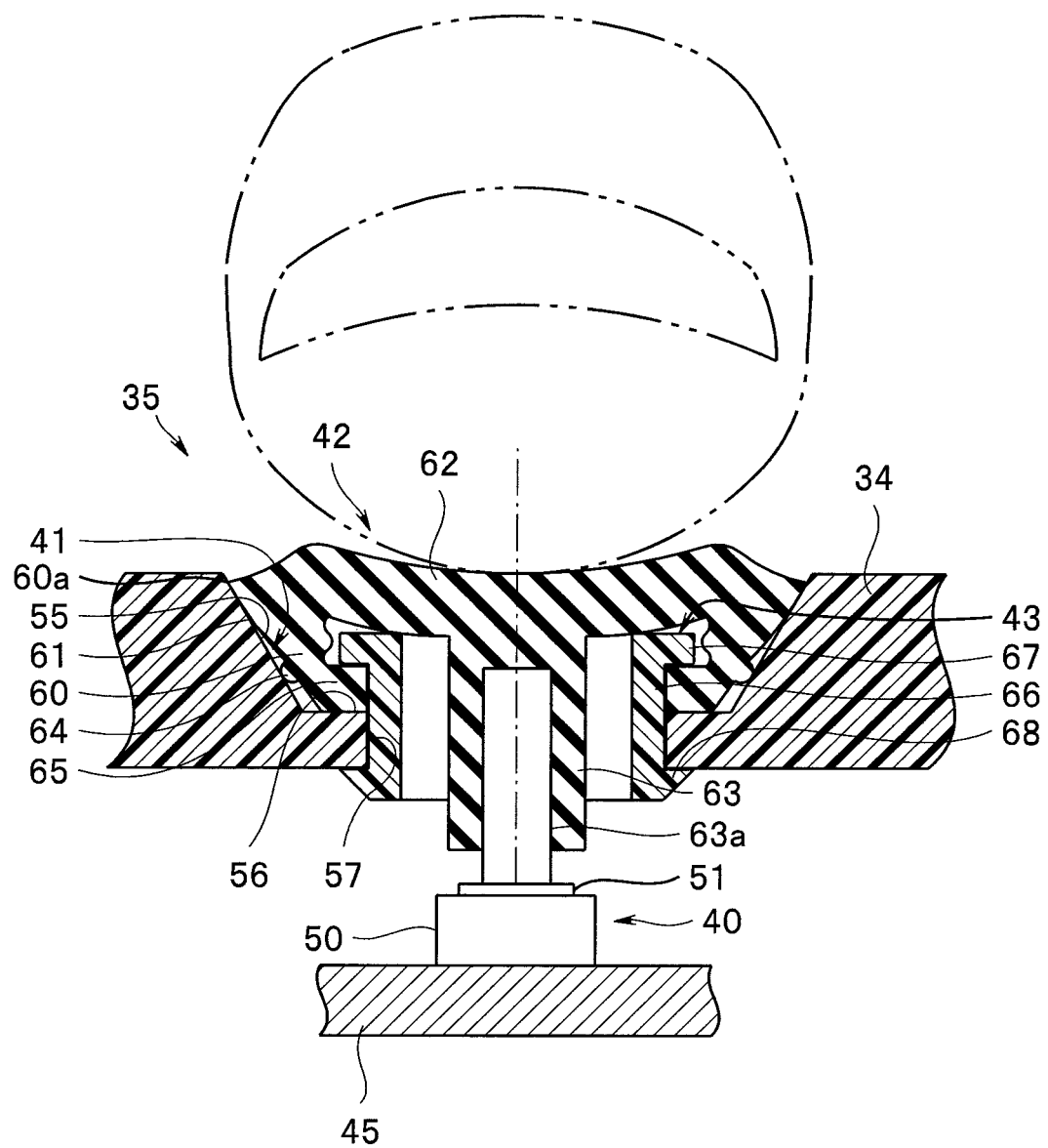
FIG. 5 is an operation explanatory view when pressing an operation button of the operation switch.
Figure 6:
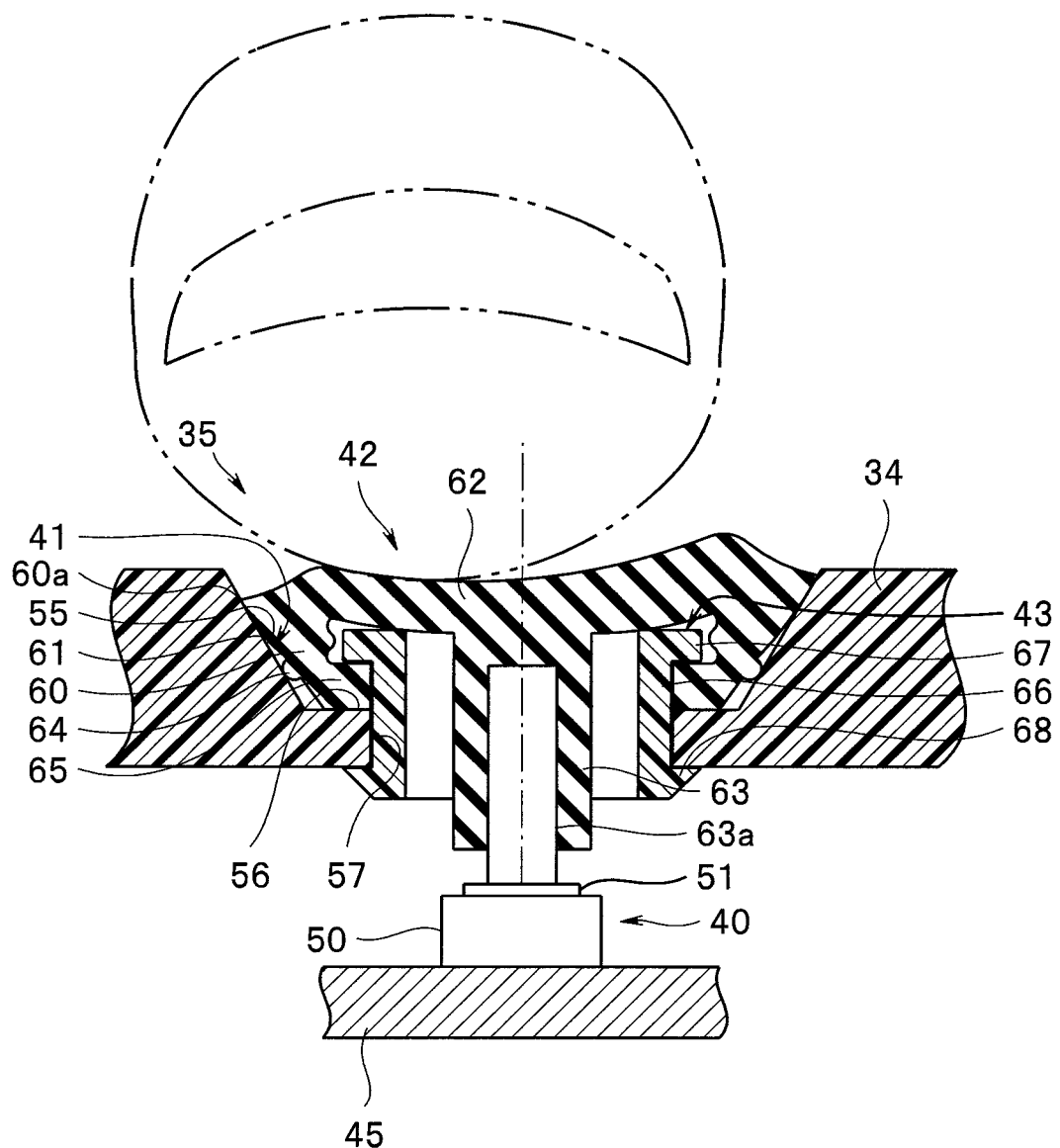
FIG. 6 is an operation explanatory view when pressing the operation button of the operation switch.

Hereinafter, an embodiment of the present invention will be described with reference to the accompanying drawings. In the drawings according to one embodiment of the present invention, FIG. 1 is a perspective view showing an appearance of an endoscope unit, FIG. 2 is a perspective view showing the endoscope unit in a state in which a monitor portion is raised, FIG. 3 is an exploded perspective view of an operation switch, FIG. 4 is a main-part sectional view of the operation switch, and FIGS. 5 and 6 are operation explanatory views when pressing an operation button of the operation switch.

Figure 1:
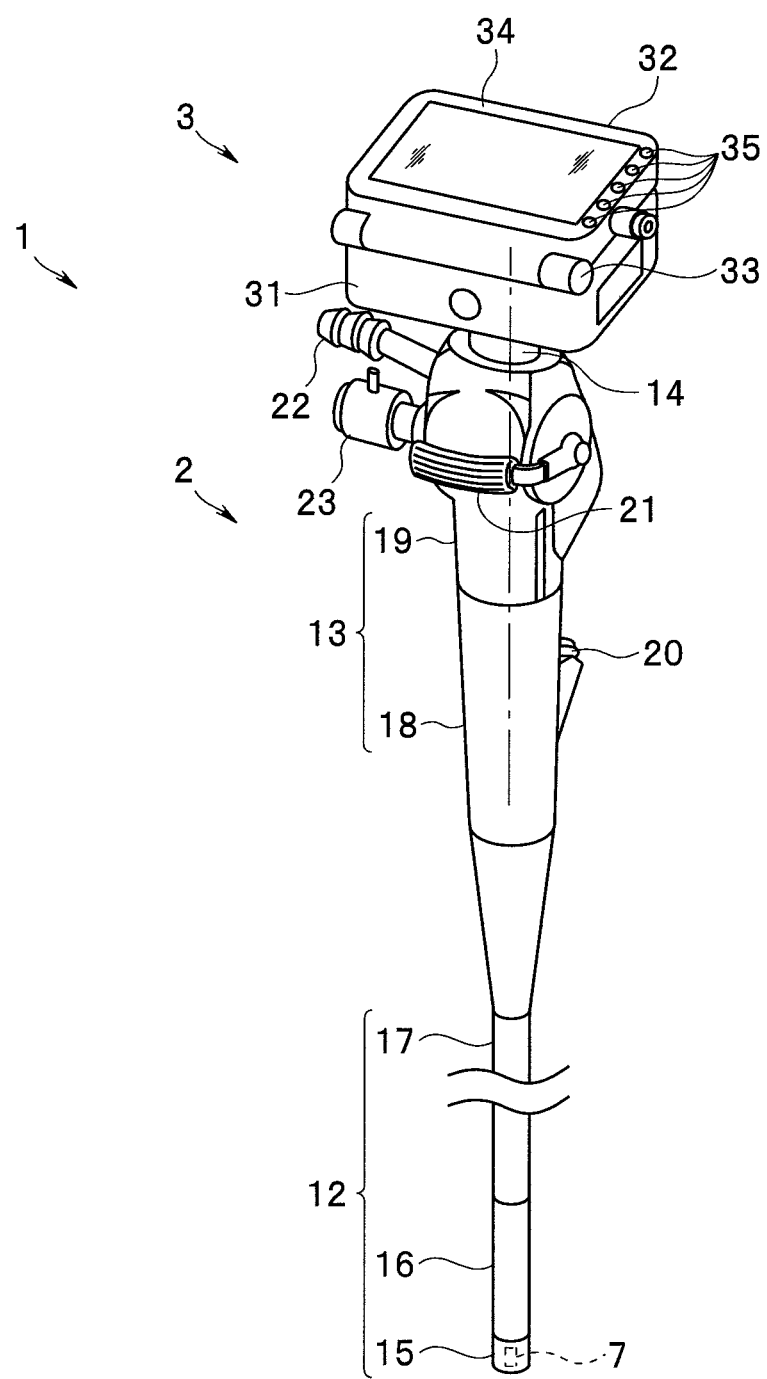
FIG. 1 is a perspective view showing an appearance of an endoscope unit.
Figure 2:
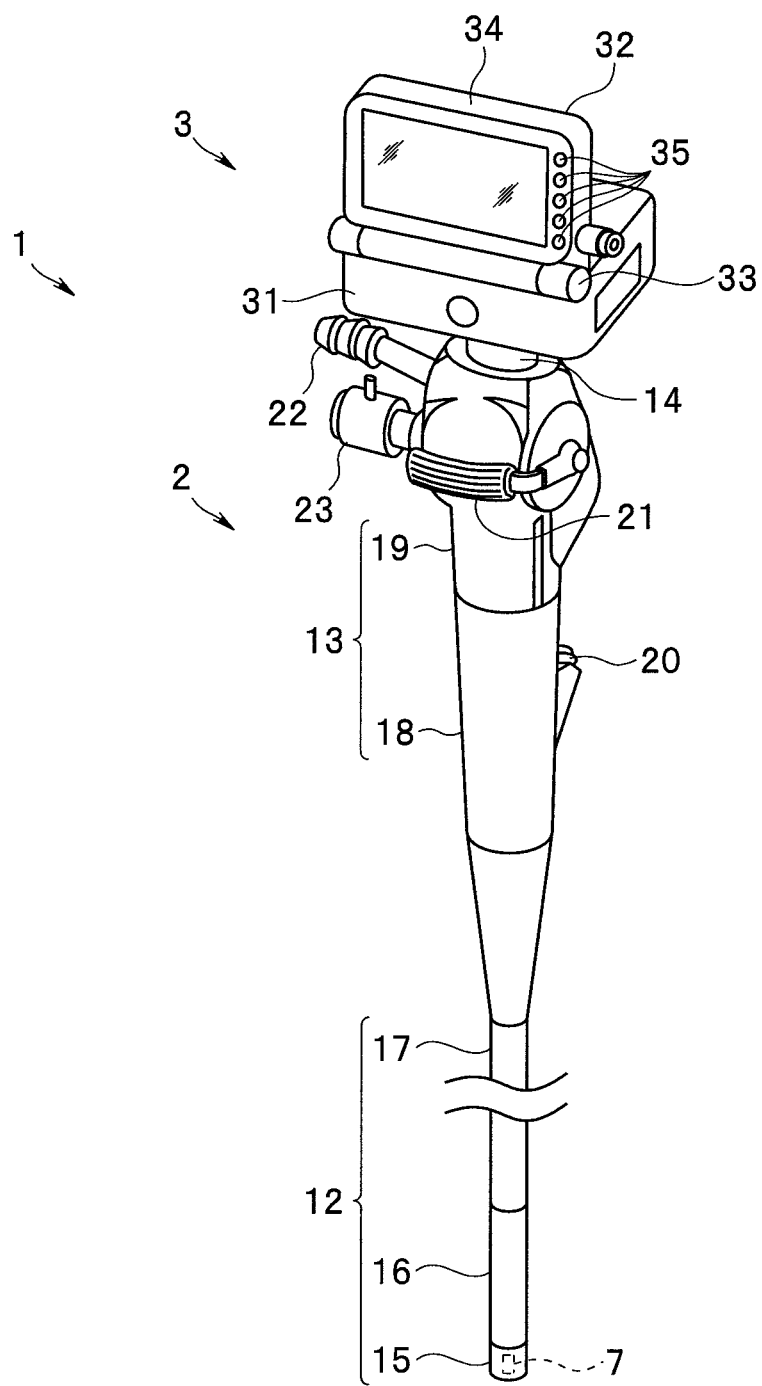
FIG. 2 is a perspective view showing the endoscope unit in a state in which a monitor portion is raised.

The endoscope unit 1 shown in FIGS. 1 and 2 is a so-called mobile scope that can be used in an ambulance car etc. The endoscope unit 1 includes an endoscope 2 and a display apparatus 3 coupled to the endoscope 2.

The endoscope 2 includes a long insertion portion 12 inserted into a subject, an operation portion 13 continuously provided at a proximal end of the insertion portion 12, and a mount portion 14 provided on a proximal end side of the operation portion 13.

The insertion portion 12 includes a distal end portion 15 in which an image pickup portion 7 is provided inside, a bending portion 16 continuously provided at a proximal end of the distal end portion 15, and a flexible tube portion 17 continuously provided at a proximal end of the bending portion 16.

The operation portion 13 includes a grasping portion 18 grasped by a user such as an operator and an operation portion main body 19 continuously provided at a proximal end of the grasping portion 18.

A treatment instrument insertion port 20 for inserting a treatment instrument such as a forceps into a not-shown treatment instrument channel inserted into the insertion portion 12 is provided in the grasping portion 18.

A bending operation lever 21 for bending the bending portion 16, for example, in an up-and-down direction is provided in the operation portion main body 19.

Further, a mouthpiece for suction 22 used when sucking a liquid such as a body fluid from a subject is provided in the operation portion main body 19. A suction apparatus can be connected to the mouthpiece for suction 22 through a not-shown tube.

Further, a mouthpiece 23 in which a check valve (not shown) released when an internal pressure of the endoscope 2 is higher than an atmospheric pressure is housed is provided in the operation portion main body 19.

The mount portion 14 is constituted by a substantially column-shaped member rotatable around a longitudinal axis of the operation portion main body 19. The display apparatus 3 serving as a coupling device for endoscope can be coupled to the mount portion 14.

The display apparatus 3 includes a display apparatus main body 31 coupled to the mount portion 14.

For example, a battery that can be taken out, an image processing control substrate, a memory socket that can mount a storage medium, and the like (not any is shown) are arranged in the display apparatus main body 31.

Further, a monitor portion 32 is coupled to the display apparatus main body 31 through a rotation axis 33. In the monitor portion 32, a plurality of operation switches 35 for performing operations of various functions of on-off of a power supply, still picture recording, moving picture recording, and the like are provided on a frame 34 that is an exterior member of the monitor portion 32.

As shown in FIGS. 3 and 4, the operation switch 35 includes a switch member 40 provided in an internal space of the frame 34, a concave portion 41 formed in the frame 34, a pressing type operation button 42 mounted in the concave portion 41, and a holding member 43 for holding an operation buttons 42 on the frame 34.

The switch member 40 is mounted on a substrate 45 such as the image processing control substrate housed in the monitor portion 32. The switch member 40 is composed of, for example, a tactile switch including a push plate 51 that projects from a switch member main body 50. When the push plate 51 is pressed, a movable contact and a fixed contact (either is not shown) provided in the switch member main body 50 are electrically connected to each other.

In a position corresponding to the switch member 40, the concave portion 41 is concaved on an external surface side of the frame 34. As shown in FIG. 3, for example, the concave portion 41 has a substantially circular shape in plan view (when viewed from the external surface side). An inner peripheral surface 55 of the concave portion 41 is constituted by a first inclined surface (a tapered surface) that is reduced in diameter toward a bottom portion 56 from an external surface.

Further, in the bottom portion 56 of the concave portion 41, in a position corresponding to the push plate 51 of the switch member 40, a communication hole 57 that cause the concave portion 41 to communicate with the internal space of the frame 34 is formed.

Here, the frame 34 according to the present embodiment is a resin-molded article and a slight inclination (taper) for easily performing demolding from molding at the time of manufacturing is normally formed in a concave portion, a convex portion, or the like formed in the above resin-molded article. Focusing on this point, in the concave portion 41 according to the present embodiment, an inclination required when forming the frame 34 is directly used, which means that the inner peripheral surface 55 is constituted by the first inclined surface without performing post processing or the like.

In other words, in the frame 34 according to the present embodiment, a first inclination required for the inner peripheral surface 55 of the concave portion 41 can be previously formed in the molding and the first inclination can serve as an inclination for the demolding, which allows the first inclination to be formed in the inner peripheral surface 55 of the concave portion 41 without adding processing after the formation. Note that it is considered that at least about two degrees are required for an inclination for the demolding, and the inclination of the inner peripheral surface 55 of the concave portion 41 is desirably set, for example, in a range of 2 to 10 degrees.

The operation button 42 includes a cylindrical portion 60 arranged so that an outer peripheral surface 61 faces the inner peripheral surface 55 of the concave portion 41, a button head portion 62 continuously provided at one end of the cylindrical portion 60, and a pressing portion 63 that projects from a rear surface side of the button head portion 62 so as to penetrate the inside of the cylindrical portion 60. The operation button 42 is made of a member more flexible than a member of the frame 34 and more specifically, respective portions configuring the operation button 42 are integrally formed by rubber having elasticity such as silicon rubber.

The cylindrical portion 60 has a substantially circular shape in plan view. The outer peripheral surface 61 of the cylindrical portion 60 is constituted by a second inclined surface (tapered surface) that is reduced in diameter toward a distal end side (the other end side) from a proximal end side (one end side) that is a button head portion 62 side.

Here, a gradient of the second inclined surface configuring the outer peripheral surface 61 of the cylindrical portion 60 is set to a gradient or more of the first inclined surface configuring the inner peripheral surface 55 of the concave portion 41. According to the present embodiment, specifically, the gradient of the second inclined surface is set slightly larger than the gradient of the first inclined surface, for example, in a range of 2 to 10 degrees.

Further, as described above, the outer peripheral surface 61 of the cylindrical portion 60 is constituted by the second inclined surface. Accordingly, a thickness of the cylindrical portion 60 is set so as to gradually become larger toward the proximal end side than the distal end side.

Here, a maximal value (that is, the outer diameter on the proximal end side of the cylindrical portion 60) of the outer diameter of the cylindrical portion 60 is set to a maximal value (that is, the inner diameter on the external surface side of the concave portion 41) or more of an inner diameter of the concave portion 41. Thereby, the operation button 42 is housed in the concave portion 41 in a state in which an edge portion 60a on the proximal end side of the cylindrical portion 60 is brought into sliding contact with the inner peripheral surface 55 of the concave portion 41.

Near to a distal end of the cylindrical portion 60, the convex portion for sealing 64 that is projectingly provided circumferentially is formed on the outer peripheral surface 61. When the operation button 42 is held in the frame 34 by the holding member 43, the convex portion for sealing 64 is set so as to pressure-contact with the inner peripheral surface 55 of the concave portion 41 while elastically deformed. Thereby, the convex portion for sealing 64 can seal the communication hole 57 formed in the bottom portion 56 of the concave portion 41 in a liquid-tight manner.

Further, an inwardly directed flange 65 facing the bottom portion 56 of the concave portion 41 is integrally formed at the distal end of the cylindrical portion 60. Note that an inner diameter of the inwardly directed flange 65 is set to be substantially the same as an inner diameter of the communication hole 57.

The button head portion 62 is configured, for example, by a substantially disk-shaped member having slight protrusion on the external surface side and is arranged so as to block the concave portion 41.

The button head portion 62 can be elastically deformed when pressed and operated by fingers etc. of a user, and on the occasion, transmits a part of a pressing force transmitted to the button head portion 62 to the cylindrical portion 60. Thereby, the button head portion 62 presses the outer peripheral surface 61 of the cylindrical portion 60 to the inner peripheral surface 55 of the concave portion 41 so that the convex portion for sealing 64 is caused to be further attached firmly to the inner peripheral surface 55 of the concave portion 41.

The pressing portion 63 is constituted by a substantially column-shaped member having a core material 63a embedded therein. A distal end side of the pressing portion 63 is inserted into the communication hole 57 formed in the bottom portion 56 of the concave portion 41. Thereby, the distal end side of the pressing portion 63 projects into the frame 34 and faces the push plate 51 of the switch member 40.

Further, when the button head portion 62 is pressed and elastically deformed by the fingers etc. of the user, the pressing portion 63 can push the push plate 51 and turn on the switch member 40.

In the holding member 43, a main part is configured using as a main body a color portion 66 having a substantially cylindrical shape. An outwardly directed flange 67 that can be engaged with the inwardly directed flange 65 formed in the cylindrical portion 60 of the operation button 42 is integrally formed at a proximal end of the color portion 66. On the other hand, a plurality of slits 66a extending in a central axis direction are provided on a distal end side of the color portion 66. Further, a nail portion 68 that can be engaged with the communication hole 57 of the concave portion 41 is integrally formed at the distal end of the color portion 66.

While the inwardly directed flange 65 is caused to be elastically deformed, the outwardly directed flange 67 of the holding member 43 is inserted into the cylindrical portion 60 to thereby be engaged with the inwardly directed flange 65. Further, while the color portion 66 is caused to be elastically deformed in the slit 66a, the nail portion 68 of the holding member 43 is inserted into the communication hole 57 to thereby be engaged with the bottom portion 56 of the concave portion 41.

Further, by an engagement between the outwardly directed flange 67 and the nail portion 68, the operation button 42 is held in the concave portion 41 of the frame 34 via the holding member 43.

In the above configuration, as shown in FIG. 5, for example, when the button head portion 62 of the operation button 42 is pressed by the user such as the operator etc., while elastically deformed, the button head portion 62 causes the pressing portion 63 to be displaced to the switch member 40 side. Thereby, the push plate 51 of the switch member 40 is pressed by the pressing portion 63 and the operation switch 35 is turned on.

On the occasion, a part of the pressing force to the button head portion 62 is transmitted also to the cylindrical portion 60, the cylindrical portion 60 is elastically deformed in the concave portion 41 by the transmitted pressing force, and the edge portion 60a of the cylindrical portion 60 is pushed into the bottom portion 56 side. However, the outer peripheral surface 61 of the cylindrical portion 60 is constituted by the second inclined surface having a gradient larger than a gradient of the first inclined surface configuring the inner peripheral surface 55 of the concave portion 41, and therefore the edge portion 60a formed at a proximal end of the cylindrical portion 60 can be always brought into sliding contact with the inner peripheral surface 55 of the concave portion 41. Accordingly, even if the edge portion 60a is displaced to the bottom portion 56 side in the concave portion 41 by the elastic deformation of the cylindrical portion 60, a foreign substance can be prevented from entering a gap between the concave portion 41 and the operation button 42.

In this case, as shown in FIG. 6, for example, even if the button head portion 62 of the operation button 42 is pressed from a biased position against a center and the cylindrical portion 60 is distorted into an unreasonable shape, a displacement of the edge portion 60a due to the pressing is a displacement in a direction in which the inner peripheral surface 55 (the first inclined surface) of the concave portion 41 is reduced in diameter. Accordingly, even in the above case, the entire circumference of the edge portion 60a can be accurately brought into sliding contact with the inner peripheral surface 55 of the concave portion 41 and a foreign substance can be prevented from entering a gap between the concave portion 41 and the operation button 42.

Here, the cylindrical portion 60 has a larger thickness on the proximal end side than a thickness on the distal end side, and therefore an excessive deformation of the cylindrical portion 60 can be suppressed in the vicinity of the edge portion 60a. Thus, the edge portion 60a can be more adequately brought into sliding contact with the inner peripheral surface 55 and a foreign substance can be prevented from entering a gap between the concave portion 41 and the operation button 42.

Note that in a case in which the button head portion 62 is released from the pressing, the operation button 42 is restored to an original shape and turns off the switch member 40. On the occasion of the restoration, the edge portion 60a of the cylindrical portion 60 is displaced up to an original position while sliding on the inner peripheral surface 55 of the concave portion 41. Accordingly, even if a foreign substance is attached to the inner peripheral surface 55 of the concave portion 41 exposed from the operation button 42 at the time of the pressing operation, the foreign substance does not remain on the inner peripheral surface 55 but is swept out by the edge portion 60a.

On the basis of the above, a foreign substance can be adequately prevented from remaining around the button head portion 62 or the like and cleaning of the display apparatus 3 or the like can be easily realized.

In addition, as shown in FIG. 6, for example, even if the operation button 42 is pressed from the biased position, the outer peripheral surface 61 constituted by the second inclined surface is displaced along the inner peripheral surface 55 constituted by the first inclined surface. Thereby, the cylindrical portion 60 (and the pressing portion 63) is centered with respect to the concave portion 41 (and the communication hole 57) and therefore the switch member 40 can be caused to be adequately operated via the pressing portion 63.

As described above, the operation switch 35 according to the present embodiment includes the concave portion 41 in which the inner peripheral surface 55 is constituted by the first inclined surface that is reduced in diameter toward the bottom portion 56 from the external surface of the frame 34 and the cylindrical portion 60 that is formed in the pressing type operation button 42 mounted on the concave portion 41 and in which the outer peripheral surface 61 is constituted by the second inclined surface that has a gradient larger than a gradient of the first inclined surface and faces the inner peripheral surface 55 of the concave portion 41. Consequently, even if the operation button 42 having elasticity, which integrally includes the convex portion for sealing 64, is operated from the biased position, the switch member 40 can be caused to adequately operate and a foreign substance can be prevented from entering. In other words, as compared with a case in which the outer peripheral surface 61 of the cylindrical portion 60 is constituted by a cylindrical surface having no inclination, or the like, the switch member 40 can be caused to adequately operate and a foreign substance can be prevented from entering.

Figure 7:
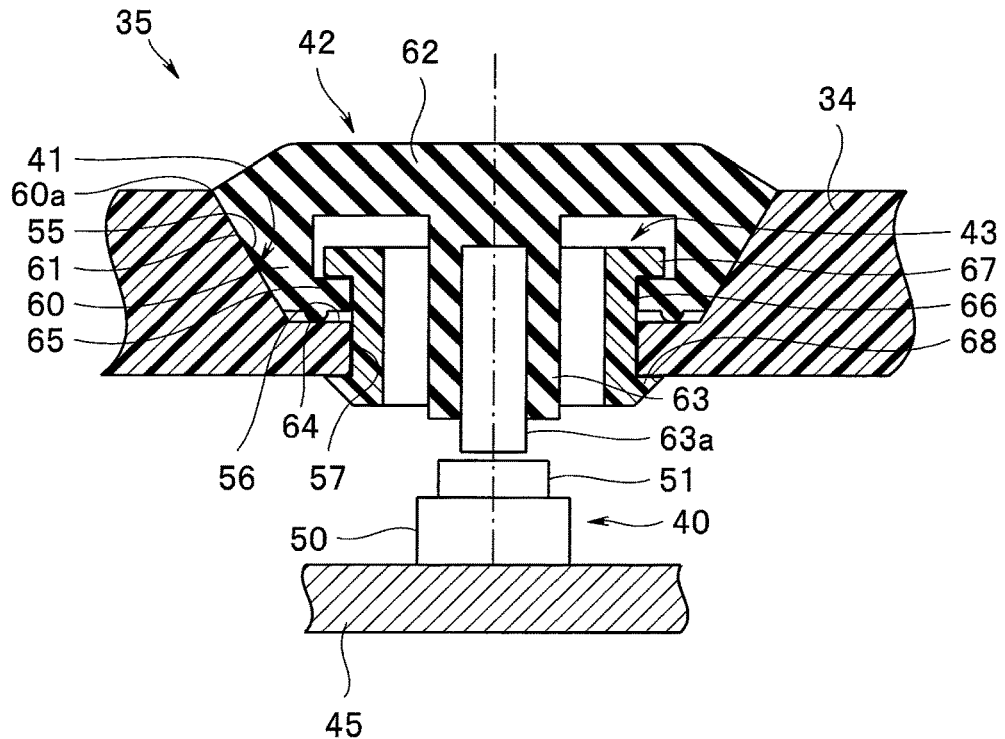
FIG. 7 is a main-part sectional view of an operation switch according to a first modification.

Here, as shown in FIG. 7, for example, instead of the second inclined surface configuring the outer peripheral surface 61 of the cylindrical portion 60, an inclined surface having the same gradient as a gradient of the first inclined surface configuring the inner peripheral surface 55 of the concave portion 41 can be used. Further, instead of the outer peripheral surface 61 of the cylindrical portion 60, the convex portion for sealing 64 can be peripherally provided at the inwardly directed flange 65 configuring a distal end surface of the cylindrical portion 60.

Figure 8:
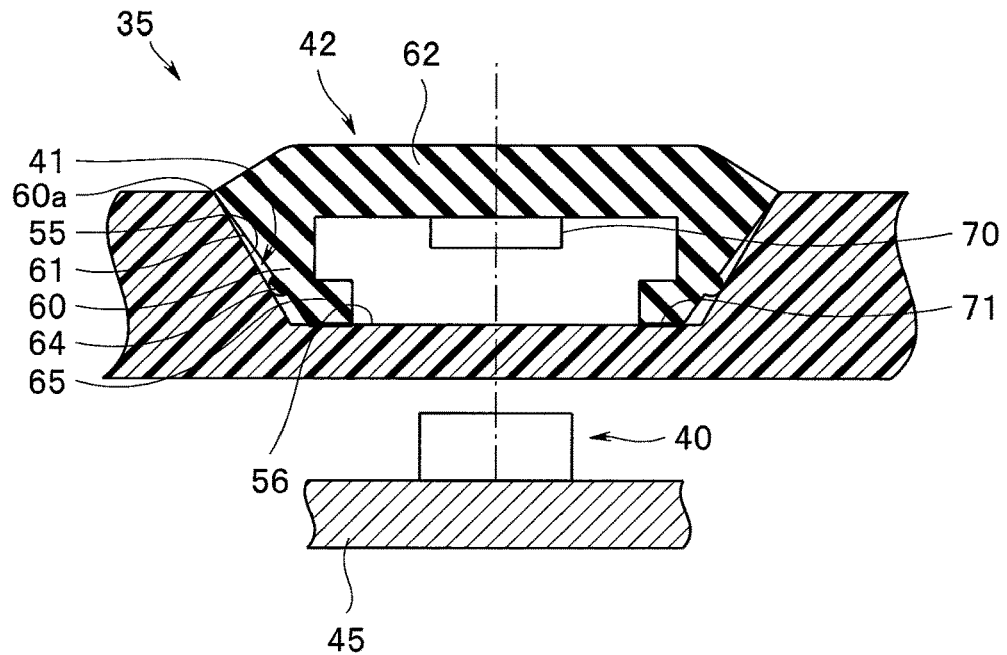
FIG. 8 is a main-part sectional view of an operation switch according to a second modification.

Further, as shown in FIG. 8, for example, the switch member 40 can be constituted by a magnetic switch instead of the tactile switch. In the case, a magnetic body 70 such as a magnet is fixed on the rear surface side of the button head portion 62. Further, when the button head portion 62 is elastically deformed by the pressing operation and the magnetic body 70 gets close to the switch member 40, the switch member 40 can detect a magnetic force from the magnetic body 70 and can be turned on.

Here, in a case in which the switch member 40 is constituted by the magnetic switch as described above, it is unnecessary to provide the communication hole in the bottom portion 56 of the concave portion 41. Then, the operation button 42 according to the present modification is fixed to the concave portion 41 by adhesive bonding without using an engaging member or the like. In the case, an adhesive portion 71 that adheres the operation button 42 to the concave portion 41 is desirably set on an inside relative to the convex portion for sealing 64. To solve the above problem, in an example shown in FIG. 8, the convex portion for sealing 64 is projectingly provided with respect to the outer peripheral surface 61 of the cylindrical portion 60. Further, the adhesive portion 71 is provided on the inwardly directed flange 65 provided at the distal end of the cylindrical portion 60.

Note that the present invention is not limited to the above-described embodiment and the like, and various modifications and changes are possible. The modifications and changes are also within the technical range of the present invention.

In the embodiment described above, for example, one example in which the operation switch 35 of the present invention is applied to the display apparatus 3 coupled to the endoscope 2 is described. However, the coupling device for endoscope to which the present invention is applied is not limited to the display apparatus 3. For example, in a case in which the endoscope is a fiberscope in which an image guide is inserted into the insertion portion, the operation switch 35 of the present invention can be applied to the image pickup apparatus coupled to the endoscope.

Figure 9:
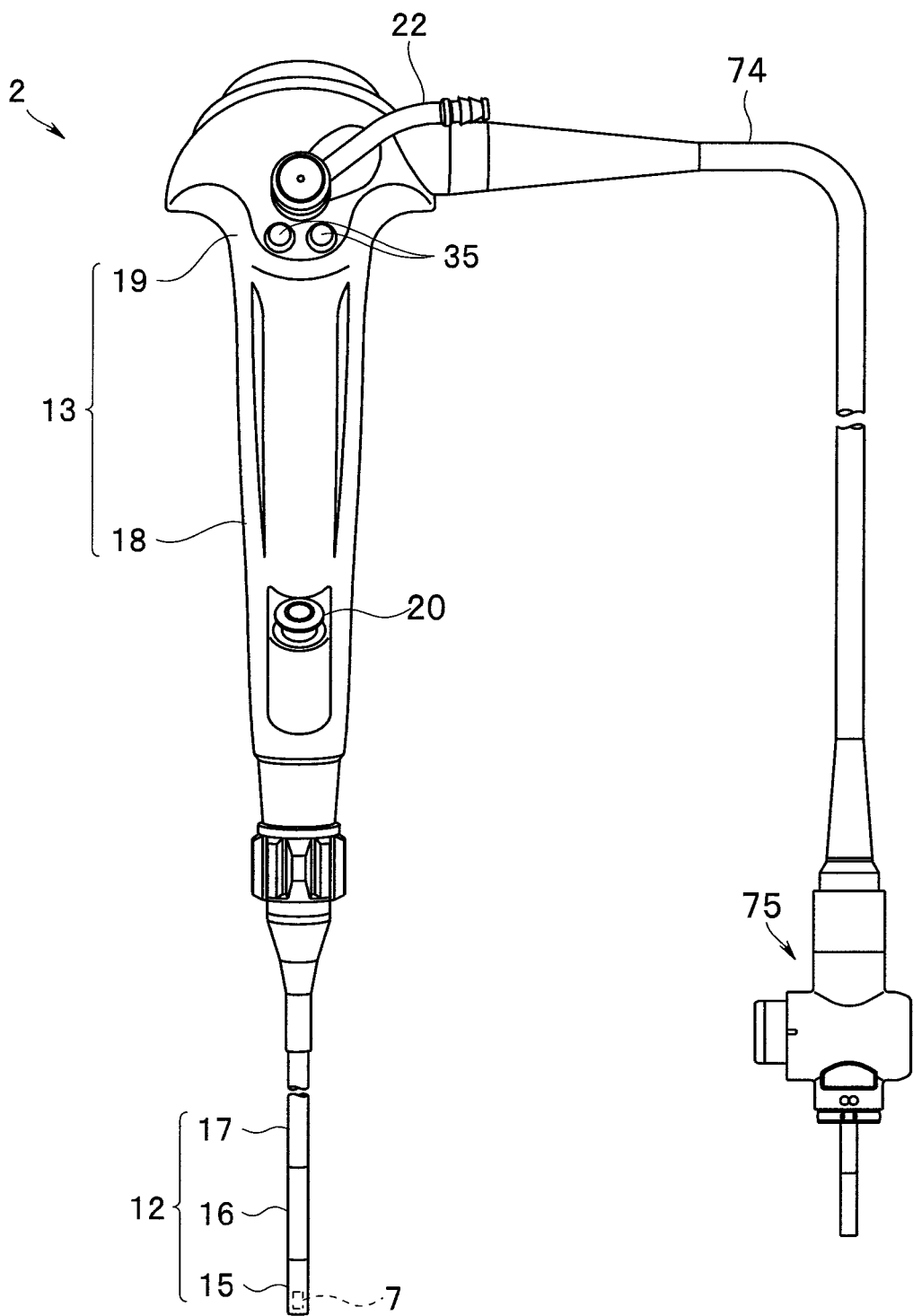
FIG. 9 is a front view showing an appearance of an endoscope to which the operation switch is applied.

Further, as shown in FIG. 9, for example, the operation switch 35 of the present invention can be applied also to the endoscope 2. Note that, instead of the mount portion 14, the endoscope 2 shown in FIG. 9 includes a universal cable 74 extended from the operation portion main body 19. Accordingly, the endoscope 2 can be connected to an external apparatus such as a control apparatus or a lighting apparatus arranged in an operating room or the like via a connector 75 provided at an extension end of the universal cable 74.

Further, needless to say that the configurations in the above-described embodiment or modifications may be appropriately combined.

What is claimed is:

1. An operation switch comprising: a concave portion provided in an endoscope or an exterior member of a coupling device for endoscope in which a switch member is housed, the concave portion including, as an inner peripheral surface, a first inclined surface reduced in diameter toward a bottom portion from an external surface; a cylindrical portion formed on a pressing type operation button housed in the concave portion, the cylindrical portion including a second inclined surface on an outer peripheral surface, the second inclined surface facing the first inclined surface and being reduced in diameter by a gradient not less than a gradient of the first inclined surface in a same direction as a direction of the first inclined surface; and a convex portion for sealing in an annular shape, the convex portion for sealing projecting from the cylindrical portion and abutting on the concave portion; wherein the operation button includes a button head portion displaceable by a pressing operation, and when the pressing operation is performed, the button head portion presses the second inclined surface against the first inclined surface so that the convex portion for sealing is attached tightly to the concave portion.

2. The operating switch according to claim 1, wherein the operation button is formed by rubber having elasticity.

3. The operation switch according to claim 1, wherein
a communication hole that communicates with an internal space of the exterior member is provided in the bottom portion of the concave portion,
the operation button includes a pressing portion that is inserted into the communication hole and transmits a pressing force with respect to the button head portion to the switch member, and
the cylindrical portion is held by the exterior member via a holding member engageable with the communication hole.

4. The operation switch according to claim 1, wherein
the operation button includes a magnetic body fixed to the button head portion,
the switch member is constituted by a magnetic switch that detects a magnetic force of the magnetic body, and
an inside of the cylindrical portion relative to the convex portion for sealing is fixed to the concave portion through adhesion.

5. The operation switch according to claim 1, wherein
the cylindrical portion has a larger thickness on a side of the external surface than a thickness on a side of the bottom portion.

6. The operation switch according to claim 1, wherein
in the cylindrical portion, the second inclined surface having a gradient larger than the gradient of the first inclined surface with respect to the external surface is formed on the outer peripheral surface, and
the convex portion for sealing is formed so as to project from the outer peripheral surface.

7. The operation switch according to claim 1, wherein
in the cylindrical portion, the second inclined surface having a same gradient as the gradient of the first inclined surface with respect to the external surface is formed on the outer peripheral surface, and
the convex portion for sealing is formed so as to project from a distal end surface of the cylindrical portion facing the bottom portion of the concave portion.

8. The operation switch according to claim 1, wherein
a maximal value of an outer diameter of the cylindrical portion is set to a maximal value or more of an inner diameter of the concave portion.

9. An operation switch comprising: a concave portion provided in an endoscope or an exterior member of a coupling device for endoscope in which a switch member is housed, the concave portion including, as an inner peripheral surface, a first inclined surface reduced in diameter toward a bottom portion from an external surface; a cylindrical portion formed on a pressing type operation button housed in the concave portion, the cylindrical portion including a second inclined surface on an outer peripheral surface, the second inclined surface facing the first inclined surface and being reduced in diameter by a gradient not less than a gradient of the first inclined surface from one end on a side of the external surface in slide contact with the first inclined surface toward another end on a side of the bottom portion; and a convex portion for sealing in an annular shape, the convex portion for sealing projecting from the cylindrical portion and abutting on the concave portion; wherein the operation button includes a button head portion displaceable by a pressing operation, and when the pressing operation is performed, the button head portion presses the second inclined surface against the first inclined surface so that the convex portion for sealing is attached tightly to the concave portion.

10. An endoscope comprising: an exterior member that forms an exterior; a concave portion provided in the exterior member and including, as an inner peripheral surface, a first inclined surface reduced in diameter toward a bottom portion from an external surface; a cylindrical portion formed on a pressing type operation button housed in the concave portion, the cylindrical portion including a second inclined surface on an outer peripheral surface, the second inclined surface facing the first inclined surface and being reduced in diameter by a gradient not less than a gradient of the first inclined surface in a same direction as a direction of the first inclined surface; and a convex portion for sealing in an annular shape, the convex portion for sealing projecting from the cylindrical portion and abutting on the concave portion; wherein the operation button includes a button head portion displaceable by a pressing operation, and when the pressing operation is performed, the button head portion presses the second inclined surface against the first inclined surface so that the convex portion for sealing is attached tightly to the concave portion.

* * * * *